United States Patent [19]

Blank et al.

[11] Patent Number: 4,968,835

[45] Date of Patent: Nov. 6, 1990

[54] PROCESS FOR THE PREPARATION OF AMINOARYL-SULPHONIC ACIDS

[75] Inventors: Heinz U. Blank, Odenthal-Gloebusch; Herbert Emde, Cologne; Peter Schnegg, Odenthal, all of Fed. Rep. of Germany

[73] Assignee: Bayer Aktiengesellschaft, Leverkusen, Fed. Rep. of Germany

[21] Appl. No.: 449,660

[22] Filed: Dec. 11, 1989

Related U.S. Application Data

[63] Continuation of Ser. No. 217,801, Jul. 12, 1988, abandoned.

[30] Foreign Application Priority Data

Jul. 18, 1987 [DE] Fed. Rep. of Germany ....... 3723801

[51] Int. Cl.$^5$ ................... C07C 143/58; C07C 143/60

[52] U.S. Cl. ........................................ 562/58; 562/61; 562/70; 562/72; 562/73

[58] Field of Search ...................... 562/58, 61, 70, 72, 562/73

[56] References Cited

U.S. PATENT DOCUMENTS 4,435,336  3/1984  Emde et al. ........................... 562/58

*Primary Examiner*—Nicky Chan
*Attorney, Agent, or Firm*—Sprung Horn Kramer & Woods

[57] ABSTRACT

Aminoaryl-sulphonic acids can be prepared by reaction of arylamines and sulphuric acid at elevated temperature and under pressure, where water formed and, where appropriate, water present as water of dilution, is left in the reaction mixture until the end of the reaction.

14 Claims, No Drawings

PROCESS FOR THE PREPARATION OF AMINOARYL-SULPHONIC ACIDS

This is a continuation of application Ser. No. 217,801, filed July 12, 1988, now abandoned.

BACKGROUND OF THE INVENTION

The present invention relates to a process for the preparation of aminoaryl-sulphonic acids by reaction of arylamines and sulphuric acid at elevated temperature and under pressure.

Aromatic aminosulphonic acids can be obtained from arylamines and sulphuric acid at elevated temperature by the so-called "baking process" (Helv. Chim. Acta 15 (1932), 1372). In this, the corresponding aminoaryl-sulphonic acid is formed at elevated temperature from initially formed arylammonium hydrogen sulphates, either in substance or in an inert solvent with exclusion of water; the water is, as far as possible, rapidly and completely removed from the reaction mixture (Ind. Eng. Chem 42 (1950), 1746). This known "baking process" frequently yields dark-coloured materials with long reaction times and somewhat moderate yields, which contain aminoaryl-disulphonic acids and also isomeric aminoaryl-sulphonic acids as undesired by-products.

A process for the preparation of aminoaryl-sulphonic acids is described in EP No. 63,271, in which the conventional variation of the "baking process" is varied in that resulting water of reaction and water of dilution which is present in some cases is not, as far as possible, rapidly and completely removed from the reaction mixture but a part of this water is always left in the reaction mixture until shortly before the end of the conversion reaction and the reaction water is completely removed from the reaction batch only in the last reaction phase for completion of the reaction. This process is carried out under pressure. It shows considerable advantages compared to the conventional "baking process" described further above.

SUMMARY OF THE INVENTION

It has now surprisingly been found that further advantages are obtained when the idea of the complete and rapid removal of water from the reaction mixture as far as possible is completely discarded. The process according to the invention on the contrary comprises completely leaving the water in the reaction mixture until the end of the reaction. Maximum reaction is achieved here in the equilibrium state. It is surprising that this equilibrium state provides a high transformation of the arylamine. On technical/economic grounds, in particular for shortening the reaction time, the reaction can also, however, be ended, before reaching the equilibrium state.

The present invention therefore relates to a process for the preparation of aminoaryl-sulphonic acids by reaction of arylamines and sulphuric acid at elevated temperature and under pressure, which is characterized in that the water formed and, where appropriate, water present as water of dilution, is left in the reaction mixture until the end of the reaction.

DETAILED DESCRIPTION OF THE INVENTION

It is therefore the distinguishing characteristic of the process according to the invention that it is performed in a closed reaction system under pressure and during the reaction no water is removed from the reaction mixture. Water here may be taken to mean the reaction water formed in a known manner from the reaction of arylamines and sulphuric acid and also, where appropriate, additionally introduced water of dilution.

The pressure for carrying out the process according to the invention may be taken to mean at least the intrinsic pressure of the reaction mixture which is developed corresponding to the progress of the reaction. An independent pressure can, of course, be superimposed on this intrinsic pressure in a manner familiar to the expert, for example by pressurizing with nitrogen, noble gases or other inert gases with reference to the reaction. The preferred driving method consists in the sole use of the intrinsic pressure developed corresponding to the progress of the reaction.

The intrinsic pressure developed, being the least under which the process is performed, may be illustrated, for example, as follows: in the reaction of aniline with sulphuric acid in o-dichlorobenzene at 200° C., the intrinsic pressure of the o-dichlorobenzene is established at 2.6 bar; if the reaction is now carried out with the addition of the mentioned reaction components, a pressure is developed by the resulting reaction water at the said 200° C., which quickly exceeds the pressure of 2.6 bar and which finally reaches an end value of 6.7 bar.

The process according to the invention is performed in a temperature range from 140°–250° C., preferably 150°–230° C., particularly preferably 180°–220° C.

The process according to the invention can be performed without or with solvent. The procedure using solvent is preferred. Where appropriate, alkyl- and/or halogen-substituted aromatics, for example, may be mentioned as suitable for the case of the procedure in the presence of a solvent. Here, this may be taken to mean, for example, benzene, a naphthalene or diphenyl, each of which can carry up to four alkyl groups and/or halogen atoms, such as fluorine, chlorine or bromine, as substituents. Alkyl substituents which may be mentioned, for example, are those having 1–4, preferably 1–2, particularly preferably 1 C atom, such as methyl, ethyl, propyl, isopropyl, butyl or isobutyl. Two adjacent alkyl substituents can together also form an alkylene chain having 3–5 C atoms, such as trimethylene, tetramethylene or pentamethylene.

Such solvents can be used both individually and as mixtures, for example technical dichlorobenzene mixtures, dichlorotoluene mixtures or trichlorobenzene mixtures.

Aliphatic hydrocarbons, such as petroleum, kerosene, isododecane or decalin, and also their mixtures, can, however, also be employed as solvents.

Alkyl- and/or halogen-substituted benzenes are preferably employed as solvents. Benzenes substituted by 1–3 halogen atoms, which in addition can still carry a methyl group, are particularly preferably employed. Dichloro- and/or trichlorobenzenes and/or dichloro- and/or trichlorotoluenes are employed in a very particularly preferred manner; for example 1,2-dichlorobenzene, 1,2,4-trichlorobenzene and the technical mixture of dichlorotoluenes may be mentioned here.

The solvent is employed in an amount of 100–2000 ml, preferably 100–500 ml, per mole of arylamine. The molar ratio of sulphuric acid to arylamine is 0.5–1.5:1, preferably 0.7–1.1:1, particularly preferably 0.8–1.05:1. For example, sulphuric acid and arylamine are reacted in a molar ratio of about 1:1; the corresponding arylammonium hydrogen sulphates can also be employed for the process according to the invention in solid form, as a suspension or as a melt.

The sulphuric acid can be employed as concentrated sulphuric acid (so-called monohydrate) or as dilute sulphuric acid. In a preferred manner, sulphuric acid containing 96–100% by weight of $H_2SO_4$ and very particularly preferably the monohydrate mentioned, are employed.

In the process according to the invention arylamines of the general formula

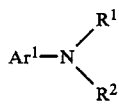 (I)

can be employed, in which $R^1$ and $R^2$ independently of one another denote hydrogen, alkyl, aralkyl or aryl or both, together with the N atom which they substitute, form a nitrogen heterocyclic ring and $Ar^1$ represents the optionally substituted benzene, naphthalene, anthracene, naphthoquinone or anthraqionone structure or the structure of an aromatic heterocyclic ring.

Alkyl which may be mentioned are those, for example, having 1–8, preferably 1–4, particularly preferably 1–2 C atoms, such as methyl, ethyl, propyl, isopropyl, butyl, isobutyl, hexyl or octyl.

Aralkyl which may be mentioned are, for example, benzyl, 1-phenyl-ethyl, 2-phenyl-ethyl, naphthyl-methyl, naphthyl-ethyl, anthryl-methyl or anthryl-ethyl, preferably benzyl.

Aryl which may be mentioned are, for example, phenyl, substituted phenyl, naphthyl or diphenyl, preferably phenyl.

For the case in which $R^1$ and $R^2$, together with the N atom which they substitute, form a heterocyclic nitrogen ring, may be mentioned those rings having 4–8, preferably 5–6 ring members, such as pyrrolidine or piperidine.

The substituted benzene, naphthalene, anthracene, naphthoquinone or anthraquinone structure can have up to 3 further substituents, for example, in addition to the amino group $-NR^1R^2$, preferably up to 2 substituents, where the substituents are arranged in such a way that at least one ortho- or para- position is unsubstituted. Examples of substituents which may be mentioned are: alkyl in the scope of the extent of meaning mentioned, phenyl or aminophenyl; halogen, such as fluorine, chlorine or bromine; furthermore hydroxyl, $C_1-C_4$-alkoxy, optionally substituted amino, $SO_3H$ or carboxyl, and also alkylsulphonyl or arylsulphonyl, such as methyl-, ethyl- or phenylsulphonyl or the optionally substituted benzothiazolyl radical. Substituents which may be preferably mentioned are methyl, ethyl, phenyl, halogen, hydroxyl, methoxy, ethoxy or amino. Substituents which may be very particularly mentioned are methyl, chlorine, bromine or fluorine.

Preferred arylamines utilizable according to the invention are those of the formula

 (II)

in which $Ar^1$ has the meaning mentioned and $R^3$ and $R^4$ independently of one another stand for hydrogen or alkyl.

Particularly preferred arylamines for the process according to the invention are those of the formula $Ar^1-NH_2$ (III)

in which $Ar^1$ has the meaning mentioned.

Additional preferred arylamines for the process according to the invention are those of the formula

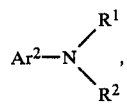 (IV)

in which $R^1$ and $R^2$ have the abovementioned meaning and $Ar^2$ represents the benzene or naphthalene structure.

Additional particularly preferred arylamines for the process according to the invention are those of the formula

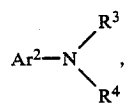 (V)

in which $R^3$, $R^4$ and $Ar^2$ possess the meanings mentioned.

In a very particularly preferred manner, arylamines of the formula $Ar^2-NH_2$ (VI)

are employed, in which $Ar^2$ possesses the meaning mentioned, and in particular, represents the benzene structure.

Examples of arylamines which can be employed in the process according to the invention are: aniline, o-toluidine, m-toluidine, p-toluidine, 2,4-dimethyl-aniline, 2,3-dimethyl-aniline, 2,6-dimethyl-aniline, 2,5-dimethylaniline, N-methyl-aniline, N-ethyl-aniline, N,N-dimethylaniline, diphenylamine, p-chloroaniline, 2,4-dichloroaniline, o-chloroaniline, 2,3-dichloroaniline, 3,5-dichloroaniline, 2,5-dichloroaniline, 2,6-dichloroaniline, m-chloroaniline, 2-amino-6-chloro-toluene, 2-amino-5-chlorotoluene, 2-amino-4-chloro-toluene, 2-methoxyaniline, 4-methoxyaniline, 2-ethoxyaniline, 4-ethoxyaniline, α-naphthylamine, p-phenylenediamine, m-phenylenediamine, aminodiphenyl, 1-amino-2-hydroxy-naphthalene, 1-amino-8-hydroxynaphthalene, 1-amino-5-hydroxy-naphthalene, 1,8-diaminonaphthalene, 1,5-diamino-naphthalene, 2-amino-3-hydroxynaphthalene, 2-amino-pyridine, 3-chloro-4-methoxyaniline, 2-amino-benzoic acid, 3,4-dichloroaniline, o-fluoroaniline, m-flluoroaniline, p-fluoroaniline, 2-amino-3-chloro-toluene, 3-amino-2-chloro-toluene, 5- amino-2-chloro-toluene, 3-amino-5-chloro-toluene, 3-amino-4-chloro-toluene, 4-amino-3-chloro-toluene, 4-amino-2-chloro-toluene, 3-amino-6-chloro-benzoic acid, aminoanthraquinones, such as, for example, 1-aminoanthraquinone or 1,5-diaminoanthraquinone, benzidine and dehydrothiotoluidine-sulphonic acid (=2-(4'-amino-phenyl)-6-methylbenzothiazole-7-sulphonic acid).

The process according to the invention can be carried out discontinuously or continuously in pressure reactors, such as autoclaves, pressure kettles, a cascade of pressure kettles or other suitable pressure reactors, such as coil or tube reactors.

The process according to the invention can be carried out, for example, in such a way that the arylamine and the sulphuric acid and also optionally co-used solvent are added in an arbitrary sequence to a pressure reactor. It is also possible to mix some or all reaction components beforehand; thus, for example, the arylamine hydrogen sulphate can be prepared beforehand and then added as such to the pressure reactor. Likewise, it is possible to mix the arylamine and the co-used solvent beforehand; this procedure is used in particular when the arylamine is solid at the temperature at which it is added to the pressure vessel. A simultaneous addition of sulphuric acid and arylamine in the above-described molar ratio is selected in particular for the continuous process. For mixing the components, static mixers or single or multisubstance nozzles having interior or exterior mixing zones are used, for example.

In a further variation, the solvent can be preheated to the reaction temperature. For this, then, the arylamine and the sulphuric acid can be added together in the form of a melt, suspension or solution or individually simultaneously or successively.

The reaction mixture obtained can be worked up in various manners. For the case in which a solution was used, it is possible, for example, to separate the aminoaryl-sulphonic acid, which is insoluble or only slightly soluble in the solvent, from the solvent by filtering off, centrifugation or similar techniques. Frequently, well-developed crystals of the aminoaryl-sulphonic acids are obtained here. In a variation thereof, water can also be added to the crystals of the aminoaryl-sulphonic acid obtained and, with the addition of a suitable base, the mixture can be converted into the more water-soluble salt form. For example, suitable bases are: sodium hydroxide, potassium hydroxide, calcium hydroxide, magnesium hydroxide, sodium carbonate, potassium carbonate, calcium carbonate, magnesium carbonate, ammonia or aliphatic amines. Sodium hydroxide or potassium hydroxide are preferably employed. This aqueous solution of a salt of an aminoaryl-sulphonic acid is then expediently freed from traces of the solvent used by incipient distillation. The clear, almost colourless salt solution of the aminoaryl-sulphonic acid thus obtained can generally be employed without any further purification. This aqueous solution can also be optionally treated, however, with suitable adsorbents, such as activated charcoal or polymeric organic adsorption agents. The aqueous solution can also be worked up, however, by evaporation to the salt of the aminoaryl-sulphonic acid dissolved in it. The aqueous solution of a salt of an aminoaryl-sulphonic acid can also be treated, however, by acidification with a mineral acid, such as hydrochloric acid or sulphuric acid, by means of which the free, very pure aminoaryl-sulphonic acid precipitates out and can be obtained as outlined above, for example by filtration.

An important working-up variation consists of adding the reaction mixture in the precipitated form to water with one of the abovementioned bases. For the case of a continuous procedure, the continuously precipitated reaction mixture can simultaneously be added with water and base or an aqueous solution of such a base to a suitable container, for example a stirring vessel. By means of this, two liquid phases are obtained, of which the organic one contains the unreacted arylamine and also optionally co-used organic solvent, whereas the aqueous phase is worked up in the above-described manner to pure salt solution, the salt itself or the free aminoaryl-sulphonic acid. The organic phase containing the unreacted arylamine can be recycled, preferably without further purification. This last-outlined working-up variation is preferred.

An advantage of the process lies in the particularly simple technical procedure, since no water is removed from the reaction mixture during the reaction, which facilitates, inter alia, a continuous procedure for the process. By the use of pressure in the process according to the invention, the choice of suitable solvents is very large. By the type of working up outlined, the total arylamine can finally be recycled and at last completely reacted by this means.

Very pure aminoaryl-sulphonic acids can be prepared with the aid of the process according to the invention. In particular, their content of undesirable aminoaryl-disulphonic acids is extremely low and in any case less than 2% by weight, less than 0.5% by weight. The aminoaryl-sulphonic acids obtainable according to the invention furthermore constitute a very pale product. This fact is of great significance, for example, for the use of aminoaryl-sulphonic acids for the preparation of optical brighteners.

In addition to further processing into optical brighteners, aminoaryl-sulphonic acids can be employed as valuable intermediates for the preparation of pharmaceuticals, foamed plastics, wetting agents, synthetic dressings, tanning substances, resists, insecticides, finishing agents, softeners and polymeric thickening agents (Ullmanns Encyclopädie der technischen Chemie (Ullmann's Encyclopaedia of Technical Chemistry), 3rd edition, Volume 16 (1965), page 561).

EXAMPLE 1

651.7 g (7.0 mol) of aniline in 1400 ml of o-dichlorobenzene were introduced into a 4 enamel stirring autoclave and 686.7 g (7.0 mol) of 100% sulphuric acid were added with stirring. The autoclave was then closed and the reaction mixture was heated to 200° C. with stirring. After 2½ hours reaction time, the reaction mixture was cooled, poured into 1000 ml of water with stirring and neutralized with sodium hydroxide solution. Two liquid phases were obtained. After replenishing the aniline to the abovementioned value, the organic phase was added to a further batch. Pure p-sulphanilic acid was obtained from the aqueous phase by acidification using sulphuric acid. The yield amounted to 64.2%.

EXAMPLE 2

The reaction was performed as in Example 1 with equivalent starting quantities, but at a temperature of 190° C. After a reaction time of 9 hours, a constant absolute pressure of 5.4 bar was attained, which indicated the attainment of the equilibrium state. After cooling, a well-crystallized residue was filtered off and dried (401.4 g). The pale grey residue from drying contained 71.1% of p-sulphanilic acid, 27.8% of aniline hydrogensulphate, 0.5% of o-sulphanilic acid and 0.1% of aniline-2,4-disulphonic acid.

EXAMPLE 3

The reaction was performed as in Example 1 with equivalent starting quantities and likewise at a temperature of 200° C. After a reaction time of 4½ hours, a constant absolute pressure of 6.7 bar was attained (equilibrium state). After cooling, the solid was filtered off and dried (400.8 g). The pale grey residue from drying contained 71.7% of p-sulphanilic acid, 25.4% of aniline hydrogensulphate, 0.5% of O-sulphanilic acid and 0.06% of aniline-2,4-disulphonic acid.

EXAMPLE 4

2-Methylaniline-4-sulphonic acid 246.4 g of 2-methylaniline in 460 ml of o-dichlorobenzene were introduced at room temperature into a 1.3 l enamel autoclave and 225.5 g of 100% sulphuric acid (monohydrate) were added. With stirring at 200° C., constant pressure was attained in the closed autoclave after just under 2 hours.

After cooling, 428 g of solid were filtered off with suction and dried. The chromatographic analysis indicated a yield of 89.5% of 2-methylaniline-4-sulphonic acid, in relation to the use of 2-methylaniline. 0.2% of 2-methylaniline-4,6-disulphonic acid was formed.

EXAMPLE 5

2-Chloroaniline-4-sulphonic acid

Starting from 293.5 g of 2-chloroaniline, 460 ml of o-dichlorobenzene and 225.5 g of monohydrate, the reaction was performed as in Example 4. After 4.3 hours at 200° C., the mixture was cooled, filtered off with suction and dried. The isolated solid weighed 489.3 g and contained 51.1% of 2-chloroaniline-4-sulphonic acid, based on the use of 2-chloroaniline, with a selectivity of 100%.

EXAMPLE 6

Naphthionic acid 329.3 g of α-naphthylamine were dissolved in 460 ml of o-dichlorobenzene in a 1.3 l enamel autoclave and 225.5 g of monohydrate was cautiously added with stirring. After closing the autoclave, the mixture was heated for 2 hours at 190° C. until the pressure was constant. The suspension obtained after cooling was filtered and the solid was dried.

The product (456.0 g) contained 34.0 % of naphthionic acid, based on the use of α-naphthylamine. The selectivity of the sulphonation amounted to 91.6%.

EXAMPLE 7 p-Sulphanilic acid 439.7 g of powdered anilinium hydrogensulphate were heated for 7 hours at 200° C. in a closed autoclave. After cooling, the autoclave was opened and the solid was dissolved in 1N NaOH (pH 7.2), deposited aniline was separated off, residual aniline was removed by extraction with methylene chloride (2×100 ml) and the aqueous phase was evaporated to dryness. The analysis of the powdery product showed a yield of p-sulphanilic acid Na salt of 68.5%, based on employed aniline. 0.7% of aniline-2-sulphonic acid and 0.02% of aniline-2,4-disulphonic acid were formed.

EXAMPLE 8 p-Sulphanilic acid 225.5 g (2.3 mol) of 100% strength sulphuric acid were added to 257.0 g (2.76 mol) of aniline in 460 ml of ortho oil. The suspension obtained was heated at 200° C. for 2.5 hours in a 1.3 l enamel autoclave. After cooling, the mixture was filtered off with suction and the filter residue was dried. The 475.6 g of solid contained 80.7% of p-sulphanilic acid in addition to unchanged anilinium hydrogensulphate, based on the excess sulphuric acid employed. Aniline-2,4-disulphonic acid was not formed.

What is claimed is:

1. In a process for the preparation of aminoarylsulphonic acids by reaction of arylamines of the formula $Ar^2$-$NH_2$ in which $Ar^2$ is optionally substituted benzene or naphthalene and sulphuric acid at elevated temperature and under pressure, the improvement wherein the process is a continuous process and wherein water formed and water present as water of dilution, is left in the reaction mixture until the end of the reaction and wherein after completion of the reaction the reaction mixture in precipitated form is added to water with an amount of a base sufficient for neutralization, the resulting organic phase is recycled in the process and the aqueous phase is used for further processing of the arylamine-sulphonic acid or worked up to give pure arylamine-sulphonic acid or its salt.

2. A process according to claim 1, wherein the reaction is carried out at a temperature of 140° to 250° C.

3. A process according to claim 2, wherein the reaction is carried out at a temperature of 150° to 230° C.

4. A process according to claim 3, wherein the reaction is carried out at a temperature of 180° to 220° C.

5. A process according to claim 1, wherein the reaction is carried out under the intrinsic pressure of the reaction mixture.

6. A process according to claim 1, wherein the reaction is carried out in the presence of a solvent or diluent.

7. A process according to claim 6, wherein a solvent is used from the group consisting of alkyl-substituted aromatics, halogen-substituted aromatics, alkyl- and halogen-substituted aromatics and aliphatic hydrocarbons.

8. A process according to claim 7, wherein a solvent is used which is a benzene, naphthalene or biphenyl each of which can carry up to four $C_1$-$C_4$-alkyl groups and/or halogen atoms whereby two adjacent alkyl substituents can together form an alkylene chain having 3–5 C atoms.

9. A process according to claim 7, wherein such solvents can be used both individually and as mixtures.

10. A process according to claim 6, wherein 100–2000 ml of solvent or diluent are employed per mole of arylamine.

11. A process according to claim 10, wherein 100–500 ml of solvent or diluent are employed per mole of arylamine.

12. A process according to claim 1, wherein 0.5–1.5 moles of sulphuric acid are employed per mole of arylamine.

13. A process according to claim 12, wherein 0.7–1.1 moles of sulphuric acid are employed per mole of arylamine.

14. A process according to claim 13, wherein 0.8–1.05 moles of sulphuric acid are employed per mole of aylamine.

* * * * *